July 25, 1950 H. C. SWIM Plant Pat. 968
ROSE PLANT
Filed April 26, 1949
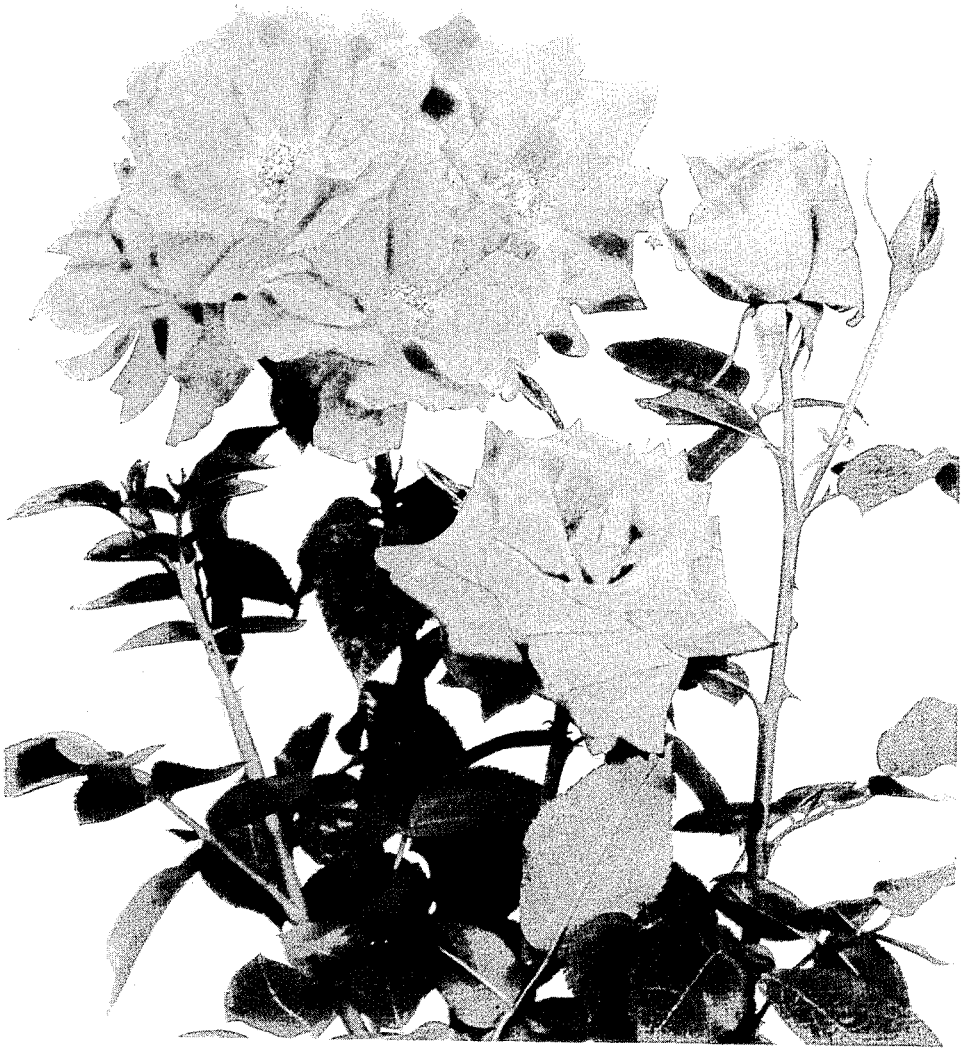
Inventor
H. C. Swim
By Robb & Robb
Attorneys Patented July 25, 1950

UNITED STATES PATENT OFFICE

968

ROSE PLANT

Herbert C. Swim, Ontario, Calif., assignor, by mesne assignments, to C. W. Stuart & Co., Newark, N. Y., a corporation of New York Application April 26, 1949, Serial No. 89,780

1 Claim. (Cl. 47—61)

The present invention relates to a new and distinct variety of rose plant having the following combination of dominating distinctive characteristics:

(1) A flower substantially equal to that of the hybrid tea class of rose in size but produced singly and in clusters with the relative freedom of the "Floribunda" or "Hybrid Polyantha."

(2) A color fastness unusual in red roses.

(3) A color value unusual in red roses and especially in a rose of this type.

This new variety differs from its seed parent "Minna Kordes" (World's Fair), Plant Patent No. 362, in the following manner:

(1) A deeper color of red in the flowers.

(2) A larger flower.

(3) A more upright, compact habit of growth.

This new variety differs from its pollen parent, "Mirandy," Plant Patent No. 632, in the following manner:

(1) It has flowers with a deeper color of red.

(2) The flowers of this new variety are semi-double, whereas those of "Mirandy" are double.

(3) The flowers of this new variety have a slight fragrance, whereas the flowers of "Mirandy"" have a very strong fragrance.

(4) This new variety is, because of its greater flower production, more satisfactory as a garden decorative variety than "Mirandy."

Asexual reproduction of this new variety shows the foregoing characteristics come true to form and are established.

The accompanying original drawings illustrate specimens of the flowers and foliage at different stages of development, as well as the single and cluster habit of blooming characteristic of this new variety.

The following is a detailed description of the new variety, all references to color being in accordance with the Robert F. Wilson Horticultural Colour Chart, 1938, except where indicated to be in accordance with Ridgway's Color Standards and Nomenclature.

This new variety was asexually reproduced at Ontario, California, by budding.

Type: Bush; outdoor; seedling; for cut flowers and garden decoration.

Class: Hybrid tea.

Breeding: Seedling.

*Seed parent.*—"Minna Kordes" (World's Fair), Pl. Pat. #362.

*Pollen parent.*—"Mirandy," Pl. Pat. #632.

Propagation: Holds its distinguishing characteristics through succeeding propagation by budding.

*Flower*

Locality where grown and following observations made: Ontario, California.

Flowers borne: Usually four to five or more to stem; in somewhat regular flat cluster; on normal, medium length to long stems.

Quantity of bloom: Free to abundant outdoors.

Continuity: Nearly continuous during growing season.

Fragrance: Slight; clove.

Bud:

*Peduncle.*—Short; average caliper; erect; rough because of numerous gland-tipped cilia. Color—Biscay Green, Plate XVII (Ridgway).

*Before calyx breaks.*—Size—medium. Form—medium length; pointed to ovate, with a few gland-tipped cilia on the surface of the bud; usually without foliaceous parts extending beyond the tip of the bud.

*As calyx breaks.*—Color—Burnt Lake, Plate XII (Ridgway).

*Sepals.*—Inner surface with tomentum; margins covered have tomentum, those that are uncovered have gland-tipped cilia.

*As first petal opens.*—Size—average to large. Form—medium length to long; flat. Color—outside: Cardinal Red, Plate 822, page 168, with shadings of Chrysanthemum Crimson, Plate 824/1, page 169; inside: Cardinal Red, Plate 822/1, page 168, with shadings of Indian Lake, Plate 826/1, page 170.

*Opening.*—Opens up well; is not retarded from opening by hot or dry weather.

Bloom: Size, when fully open—average; 3 inches to 3¾ inches.

*Petalage.*—Semi-double to double; from 18 to 24 petals; plus 3 to 6 petaloids; arranged regularly.

*Form.*—Urn-shaped at first; becoming flat to open; petals remaining at first loosely rolled outward; later at maturity lateral margins become more tightly rolled outward.

Petals:

*Texture.*—Medium thick; soft; with inside velvety and outside satiny.

*Shape.*—Outside—nearly orbicular, sometimes with mucronate tip with one to three notches. Intermediate—broadly obovate; mucronate, with none to one notch. Inside—broadly obovate, mucronate and non-mucronate tips.

*Color.*—Colors may be modified by being overlaid, shaded or tinted with other colors.

3

This description of a newly opened flower was made from a rose grown outdoors in the month of September, at Ontario, California:

*Color.—Outside petal*—outside surface: Cardinal Red, Plate 822/2, page 168, with shadings of Chrysanthemum Crimson, Plate 169, page 169; basal attachment point of Dresden Yellow, Plate 64/2, page 64; inside surface: Currant Red, Plate 821/2, page 167, shaded with Chrysanthemum Crimson, Plate 824, page 169; basal attachment point of Dresden Yellow, Plate 64/2, page 64. *Intermediate petal*—outside surface: Cardinal Red, Plate 822/1, page 168; attachment region is Primrose Yellow, Plate 601/2, page 65; inside surface: Currant Red, Plate 821/2, page 167, with shadings of Cardinal Red, Plate 822/1, page 168. Attachment region is Primrose Yellow, Plate 601/2, page 65. *Inner petal*—outside surface: Cardinal Red, Plate 822/1, page 168, with vegetative breaking, in mid-rib region extending from attachment region at petal base to one-half to all the way up the petal of Rose Bengal, Plate 25/1, page 25; inside surface: Currant Red, Plate 821/2, page 167, with shadings of Cardinal Red, Plate 822/2, page 168. Attachment region is Primrose Yellow, Plate 601/2, page 65.

This description was made from a rose that was open for three days outdoors in the month of September, at Ontario, California:

*Color.—Outside petal*—outside surface: near Chrysanthemum Crimson, Plate 824/1, page 169; inside surface: between Currant Red, Plate 821, page 167, with shadings of Chrysanthemum Crimson, Plate 824, page 169; burned tip regions appear overlaid with Purple Madder, Plate 1028, page 181. *Inside petal*—outside surface: Cardinal Red, Plate 822/1, page 168, with vegetative breaking in mid-rib region extending from attachment region at petal base one-half to all the way up the petal, of Rose Bengal, Plate 25/1, page 25; inside surface: Cardinal Red, Plate 822/1, page 168, with shadings of Chrysanthemum Crimson, Plate 824/1, page 169.

*General color effect.*—Newly opened flower—Cardinal Red, Plate 822/2, page 168, deeper shaded portions appearing Chrysanthemum Crimson, Plate 824/2, page 169. Three days open—Cardinal Red, Plate 822/2, page 168, with shadings of Chrysanthemum Crimson, Plate 824/1, page 169.

*Behavior.*—Drop off cleanly; fading to Cardinal Red, Plate 822/3, page 168; affected by hot, dry weather when petals burn slightly.

*Flower longevity.*—On bush in garden—4 to 5 days in October. Cut roses grown outdoors kept at living room temperatures—3 to 4 days in October.

*Reproductive organs*

Stamens: Average number; arranged regularly about pistils.

Filaments: Stort to long; most with anthers.

4

Color—Begonia, Plate 619/1, page 146, changing to nearly white at anther attachment region.

Anthers: Medium size; all open at once approximately. Color—central portion is nearly white shaded with Phlox Purple, Plate 632/1, page 151. Color under side—tip is Phlox Purple, Plate 632, page 151; upper side margins are Indian Yellow, Plate 6/1, page 6.

Pollen: Somewhat sparse. Color—Indian Yellow, Plate 6/1, page 6.

Pistils: Average number, approximately 50 in number.

Styles: Moderately even; average length; thin to average caliper; bunched. Color—Cardinal Red, Plate 822/3, page 168, in upper ¾ of length. Lower portions are Chartreuse Green, Plate 663/3, page 90.

Stigma: Color—Saffron Yellow, Plate 7/3, page 7, with translucent appearance.

Ovaries: Usually all enclosed in calyx.

Hips: Average length; pear-shaped to turbinate; smooth; thick; fleshy. Color—three-fourths mature hip near Oil Yellow, Plate V (Ridgway).

Sepals: From newly open flowers—permanent; medium length; spear-shaped; recurved slightly. Color—inside—basic color is Parrot Green, Plate VI (Ridgway) overlaid heavily with white tomentum, giving the appearance of Corydalis Green, Plate XLI (Ridgway); outside—Courge Green, Plate XVII (Ridgway) with darker shadings of Biscay Green, Plate XVII (Ridgway).

Seeds: Average number; usually medium size; 8 to 15 in number.

*Plant*

Foliage:

*Leaves.*—Compound usually of 5 to 7 leaflets; normal quantity; medium size; somewhat leathery and dull.

*Leaflets.*—Shape—ovate with apex acute; base round; margin serrate.

*Color.—Mature* — upper surface — Parsley Green, Plate 00962/1, page 193; under surface—between Lavender Green, Plate 000761/1, page 196, and Lavender Green, 000761, page 196. *Young*—upper surface—Calla Green, Plate V (Ridgway), edges of Mineral Red, Plate XXVII (Ridgway); under surface—Mineral Red, Plate XXVII (Ridgway) with Calla Green, Plate V (Ridgway), appearing at leaflet tips and occasionally on mid-rib.

*Rachis.*—Average size too heavy. Upper side—grooved with hair and stipitate glands on edges. Under side—prickly with stipitate glands.

*Stipules.*—Medium length; narrow to wide with moderately short points, turning out at an angle of 45° to 90°.

*Disease.*—Average resistance to mildew.

Growth:

*Habit.* — Bushy; upright; moderately branched.

*Growth.*—Moderate.

*Canes.*—Medium caliper.

*Main stems.*—Color—Parrot Green, Plate VI (Ridgway). *Large prickles*—several; medium length; hooked slightly downward; with narrow base. Color—Clay Color, Plate XXIX (Ridgway). *Small prickles and hairs*—none.

*Branches.*—Color—Turtle Green, Plate XXXII (Ridgway). *Large prickles*—several; medium length; hooked slightly downward; with narrow base. Color—Amber Yellow, Plate XVI (Ridgway). *Small prickles and hairs*—none.

*New shoots.*—Color—Grape Green, Plate XLI (Ridgway) overlaid with Vinaceous-Drab, Plate XLV (Ridgway). *Large prickles*—several; medium length to long; hooked slightly downward; with medium length narrow oval base. Color—Amber Yellow, Plate XVI (Ridgway) tinted with Corinthian Red, Plate XXVII (Ridgway). *Small prickles*—few. Color—near Corinthian Red, Plate XXVII (Ridgway). *Hairs*—none.

I claim:

A new and distinct variety of rose plant of the hybrid tea class characterized as to novelty by its habit of production of blooms of hybrid tea size both singly and in clusters with the relative freedom of blooming characteristic of the floribunda or hybrid polyantha type; the color of the flowers unique among red roses and especially in a rose of the foregoing type; and the fastness of this color of the bloom, also unusual in red roses, substantially as shown and described.

HERBERT C. SWIM.

No references cited.